United States Patent [19]
Barth et al.

[11] Patent Number: 5,143,744
[45] Date of Patent: Sep. 1, 1992

[54] DYNAMIC CONTACT ANGLE MEASUREMENT SYSTEM

[75] Inventors: Jerry J. Barth, Red Wing; Garry R. Zvan, White Bear Lake, both of Minn.

[73] Assignee: Minnesota Mining and Manufacturing Company, St. Paul, Minn.

[21] Appl. No.: 717,534

[22] Filed: Jun. 19, 1991

[51] Int. Cl.⁵ .............................................. B05D 1/26
[52] U.S. Cl. ........................................ 427/8; 118/710; 118/113; 118/715; 118/319; 427/286; 427/430.1; 427/434.2
[58] Field of Search .............. 427/8, 286, 434.2, 430.1; 118/713, 710, 789, 715

[56] References Cited
U.S. PATENT DOCUMENTS

| | | | |
|---|---|---|---|
| 3,359,938 | 12/1967 | Klemmer | 118/409 |
| 3,409,658 | 10/1968 | Damm et al. | 118/409 |
| 4,656,048 | 4/1987 | Kudoh et al. | 427/8 |
| 4,666,732 | 5/1987 | Schnucker | 427/8 |
| 4,762,727 | 8/1988 | Voswinckel | 427/8 |

*Primary Examiner*—Janyce Bell
*Attorney, Agent, or Firm*—Gary L. Griswold; Walter N. Kirn; Charles D. Levine

[57] ABSTRACT

An apparatus for measuring the dynamic contact angle of a coating on a discrete web segment includes a rotatable coating wheel around which the web segment is mounted and a syringe which produces a coating bead having no edge bead. The interface between the coating and the web is viewed in a plane parallel to the axis and the surface of the coating wheel and the contact angle is measured.

9 Claims, 3 Drawing Sheets

DYNAMIC CONTACT ANGLE MEASUREMENT SYSTEM

TECHNICAL FIELD

The present invention relates to an apparatus for measuring the dynamic contact angle of a coating wetting a substrate. More particularly, the present invention relates to an apparatus for measuring the dynamic contact angle which is convenient and accurate under actual use conditions.

BACKGROUND OF THE INVENTION

There are great differences in the way that different fluids or coatings wet out on and spread across solids. One fluid may spread out with ease on one solid but not at all on a different solid. This is due to the balance of surface energies for the system and its components. The contact angle is a measure of the degree to which a fluid wets a solid. The contact angle is measured through the fluid and is the angle between the surface of the fluid and the surface of the substrate as measured through the fluid at the contact line. Under dynamic conditions, if the angle is small, then the fluid wets and spreads across the solid readily. If it is large, then the fluid may not spread at all.

The contact angle that a fluid makes under static conditions is a measure of the relative surface energies of the solid and fluid. The contact angle that a fluid makes under dynamic coating conditions is a measure of how well the fluid "wets" or coats the substrate in competition or in concert with hydrodynamic and other forces. This is particularly true for fluids which are loaded with surface active agents, are coated on surface active solids or textured solids, or are coated with electrostatic assist, as in the photographic industry. In these environments, the observed dynamic contact angle differs from that which would be expected from a pure consideration of surface tension, hydrodynamic forces, and the contact angle measured under static conditions. Surfactants added to the fluid require a finite time to migrate to the surface and may or may not be present on the solution surface at the dynamic contact line. Also, surfactants may be present on the surface of the uncoated backing, the backing may have a distinct texture, and any electrostatic, magnetic, or other fields could affect the observed dynamic contact angle.

One measure of the competition between the surface tension forces and the hydrodynamic forces is the capillary number, which is the ratio of the viscous forces in a flow to the surface tension forces. At very low speeds and low capillary numbers the dynamic contact angle approaches the angle measured under static conditions. As the coating speed and the associated wetting speed increases, the contact angle increases. Eventually the contact angle reaches 180° and air is entrained. This is reported to occur at a capillary number of approximately one in low viscosity fluids and is consistent with the expectation that surface forces dominate the flow at low capillary number, and that higher capillary numbers indicate increasing competition from hydrodynamic forces. With higher viscosity fluids, air entrainment can occur at higher capillary numbers.

The contact angle is an important factor in the investigation of low capillary number coating flows. In these flows, the coating bead shape is dominated by surface tension. The effect of the contact angle can dominate all other aspects of the flow. This is apparent when numerical modeling of the coating flows is attempted and a dynamic contact angle is specified as an input variable.

A number of techniques for measuring the dynamic contact angle are known. In the plunging tape method, the substrate being tested is plunged into a coating fluid bath. Substrate speed is increased until the critical velocity for air entrainment is reached and a tongue of air is pulled into the fluid to entrain air bubbles. The contact angle is measured by examining the vicinity of the contact line through the side of the tank as the speed changes. However, this method requires a large pool volume and a large testing surface area as compared with the region of interest. As the flow of the fluid outside of the vicinity of the contact line is not well defined, it may not represent the coating process. Also, the age of the fluid surface is uncertain, and may mask the effects of surface active agents. If the coating fluid contains volatile components, evaporation presents additional unknown effects. Additionally, the contact angle is difficult to view as measurements are made through the transparent side of the tank. If the fluid is opaque, no angle will be visible at all. Also withdrawal of the tape from the bath tends to pull a film of the coating bath with it. Data on the contact angle taken by this method shows scatter on the order of ±4°.

A second method of observing the contact angle involves pumping fluid through a capillary tube or between parallel plates. If this device is immersed in a fluid with an index of refraction similar to the substrate, the contact angle can be determined by a combination of microscopic examination and numerical approximation. This restricts investigation to surfaces which are substantially transparent. The size of the apparatus also limits the time available to take measurements and the speed of the substrate at which a measurement is practical.

A third method involves partially submerging a turning roll in a tank of fluid. The roll may or may not be doctored clean before its surface is rotated into the fluid to observe the contact angle. This method shows smaller contact angles and higher critical speeds than the plunging tape method. The pre-wet substrate and large tank volumes make the results obtained by this method of questionable value for the study of the coating process.

Other measurements of the dynamic contact angle for coating situations have been made using specially designed slot die coaters. In die-based coating systems, the fluid is metered out of the die nozzle and onto a substrate. The die is usually close to the substrate surface, the fluid has a well defined flow field and surface history, and the contact angle can be directly measured. However, when using a full size die coater, it is difficult to access the coating bead or to align the optics to get the bead of coating fluid in profile. Also, there is always an edge bead, which obscures the undisturbed coating bead. To avoid this edge bead, a sheet of glass is commonly mounted at the end of the slot coater and the coating bead is viewed from within the coating fluid. This is not practical with opaque fluids. Finally, the aperture of the optical system observes a plurality of light rays which cause multiple internal reflections. As a result, the dimensions of the bead to be examined must be relatively large to reduce obstruction.

These known systems are inconvenient to use, are limited in their choice of coating and substrate materials, and do not provide a fluid flow field which accurately simulates that experienced in a coater.

SUMMARY OF THE INVENTION

The dynamic contact angle measurement system of the present invention uses a narrow needle that does not produce heavy edge beads or multiple reflections. The needle is mounted on the end of a syringe to coat onto a strip of web mounted on a motor-driven coating wheel. The coating wheel is spun at a surface speed equal to the speed that a particular fluid coating is typically coated. When the wheel is at the desired speed and the coating flows from the syringe, the syringe is moved into the coating position. It is left in this position and ejects coating onto the web segment until up to the entire circumference of the coating wheel is coated. A video camera observes the coating and transmits its video signal to a computer which computes the coating angle.

In an alternate embodiment, the syringe coats on a long web moving past a backup roller. The syringe is mounted to impinge the coating near the edge of the web. The web and backup roller are conventionally driven.

DETAILED DESCRIPTION OF PREFERRED EMBODIMENTS

Figure 1:
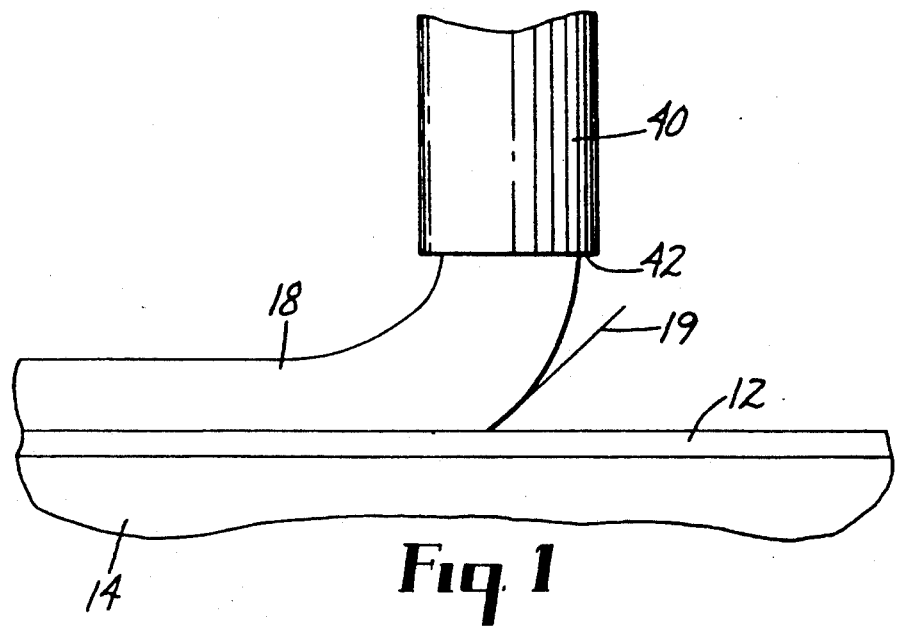
FIG. 1 is a side view of a portion of the dynamic contact angle measurement system showing the coating angle.

The system of the present invention uses a very narrow coating outlet to measure the contact angle between a fluid coating, referred to as simply a coating, and a substrate, such as a web as shown in FIG. 1. The coating outlet is usually close to the web surface and can be round, elongated, or polygonal. The coating flow field is well defined and the age of the coating surface can be controlled to match that of typical coaters. The coating may be opaque or may contain volatile components, and web speed and composition are not restricted. Dark or bright field techniques can be used to sharply contrast the coating bead silhouette for measurement. There are no confusing multiple reflections and the optics aperture is not critical because the bead is narrow. The contact angle can be directly measured in the exact configuration of interest at coating conditions.

The data obtained from this system results in more visible detail than known apparatus. This detail is apparently the result of surface dynamics which cannot be seen with the plunging tape. As the apparatus is quite sensitive to variations in backing and emulsion properties, there is good correlation between angles measured with this apparatus and plant experience which correlates run time with a statistical analysis of defect data.

Figure 2:
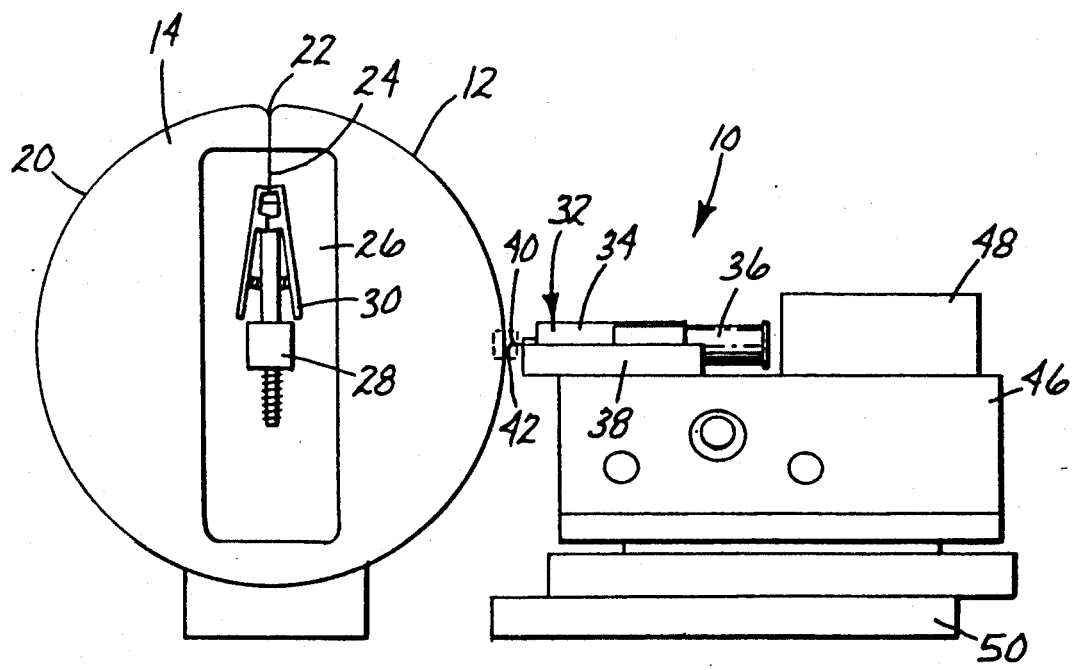
FIG. 2 is a schematic view of the dynamic contact angle measurement system according to the present invention.
Figure 3:
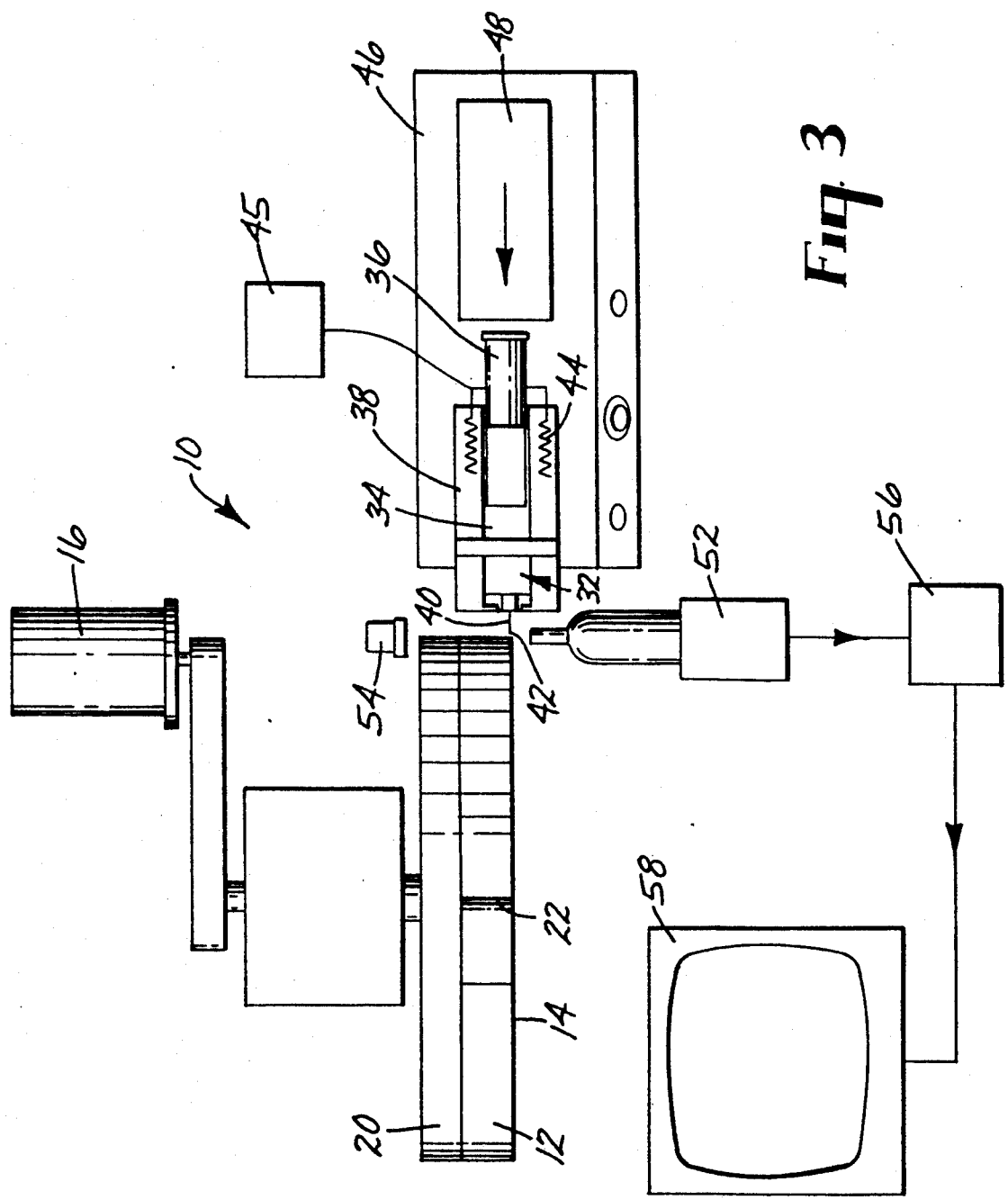
FIG. 3 is a schematic view of the dynamic contact angle measurement system of FIG. 2 showing additional components.

In the preferred embodiment shown in FIGS. 1-3, the apparatus 10 measures the dynamic contact angle. The apparatus 10 takes less time to acquire the angle than known methods. A fluid coating is coated on a substrate and the contact angle between the substrate and a line 19 tangent to the coating fluid where the coating fluid initially contacts the substrate is measured. The contact angle for the exact coating and substrate can be measured at normal coating speeds. As the angle is mostly insensitive to setup parameters and flow rates, it fairly represents what occurs in a full width coating flow.

The apparatus 10 includes a discrete web segment 12 wrapped around a coating wheel 14 which is driven by a motor 16. The coating wheel 14 is approximately 30 cm in diameter and 5.0 cm wide. The web segment 12 is not part of a long length of web moving past the coating wheel 14. Rather, the web segment 12 is a segment having a maximum length sufficient to wrap once around the circumference of the coating wheel 14 and be held in position. The web segment 12 need not wrap completely around the coating wheel 14 as this apparatus 10 attains quick coating pickup and the coating angle to be measured in a very short distance. The web segment 12 grabs the fluid coating 18 and the coating 18 adheres to the web segment 12 and forms a stabilized, consistent coating 18 almost immediately after the coating 18 is moved into position to coat on the web segment 12.

The coating wheel 14, shown in FIGS. 2 and 3, includes a smooth circumferential surface 20 interrupted by a slot 22 which receives the ends 24 of the web segment 12. The slot 22 can extend through most of the axial width of the coating wheel 14. The ends 24 are then received within a recess 26 in the coating wheel 14 which has a depth equal to the length of the slot 22. The recess 26 houses the drive connection 28 to the motor 16 and a spring-actuated clamp 30 which holds the web segment 12 in position around the circumferential surface 20. The web segment 12 is wrapped around the circumferential surface 20 of the coating wheel 14 preferably at the edge of the coating wheel 14. The coating wheel 14 is spun at a surface speed selected to match the speed that the coating 18 is typically coated.

The coating fluid 18 is delivered by a tube such as a syringe 32. The syringe 32 includes a cylinder 34 and a plunger 36 and is mounted in a syringe holder 38. A needle 40 is attached at the closed end of the cylinder 34. The needle 40 has an outlet 42 located adjacent one edge of the wheel 14. The needle outlet 42 preferably has a flat end and an opening which is chosen in combination with the properties of the coating 18. Outlet 42 sizes of up to 1.5 mm have been found to work well. Larger outlet 42 sizes can be used with higher viscosity coatings to improve flow. Additionally, one or more heaters 44 can be connected to the syringe holder 38 to warm the coating 18 in the syringe 32 to maintain the temperature of the coating 18 and maintain viscosity. Where the coating 18 is a gel or other substance which hardens when cooled, maintaining the temperature is important to optimizing flow. The heaters 44 can be built into the syringe holder 38 and extend along part or all of the length of the syringe 32. The heaters 44 are controlled by a temperature controller 45.

The syringe 32, mounted in the syringe holder 38, is mounted on a syringe pump 46. Alternatively, the needle 40 can be mounted directly to the end of a pump (not shown) or can be gravity-fed. The syringe pump 46 includes a translating pusher arm 48 which translates toward and contacts the plunger 36 of the syringe 32 to push the plunger 36 to dispense coating 18 from the syringe 32. The syringe pump 46 is mounted on a slide table 50 which is translatable toward and away from the coating wheel 14 to bring the syringe 32 into and out of position adjacent the coating wheel 14 during operation. The web segment 12 can be 90 cm long and 3.8 cm wide.

When the wheel 14 spins at the desired speed and the coating 18 flows from the syringe 32, the syringe 32 on the slide table 50 is slid into the coating position adjacent the web segment 12. The syringe pump 46 moves the syringe plunger 36 within the cylinder 34 of the syringe 32 to coat up to the entire length of the web segment 12. A close-up (60× times magnification) video recording is made of the contact area using a video camera 52 and a back light 54 shining directly past the syringe 32. The back light 54 creates a silhouette of the contact angle to provide contrast for determining the coating angle. The video camera 52 preferably views the coating angle from the side and in a plane parallel to the axis and surface of the web segment 12. The video signal is fed directly into a computer 56, which is programmed to determine the contact angle, through a frame grabber board. The computer 56 can capture and display fourteen consecutive frames of video; examine the frames, locate the contact point, and compute the contact angle; store the data; and generate reports of various runs. The video signal also is fed into a monitor 58 for viewing to assist in the calibration of the apparatus 10. Any of the fourteen frames can be displayed and printed on a hard copy unit (not shown) such as a printer. Alternatively, the video signal can be "still framed" using a video cassette recorder (not shown) for analyzing the angle from the hard copy unit.

In addition to studying the dynamic contact angle of a single coating on a dry substrate, the apparatus 10 has other uses. The effect of coating on a wet substrate can be studied if the substrate is pre-wet. If the coating is elastic, its profile drawn from the syringe can be studied regarding elastic effects. The effects of an electrostatic or other field imposed on the coating also can be studied by adding a high voltage power supply to charge the needle. The thin strip of coated material resulting from this measurement system can be used for further studies of product properties or production. Additionally, a double nozzle for coating two coatings can be used to analyze the interface between the two coatings. This configuration also can be used to measure at least the coating-web contact angle and more than two coatings can be analyzed this way. Moreover, the coating wheel can be rotated more than once, and the effect of coating a second identical layer upon the first can be studied.

Figure 4:
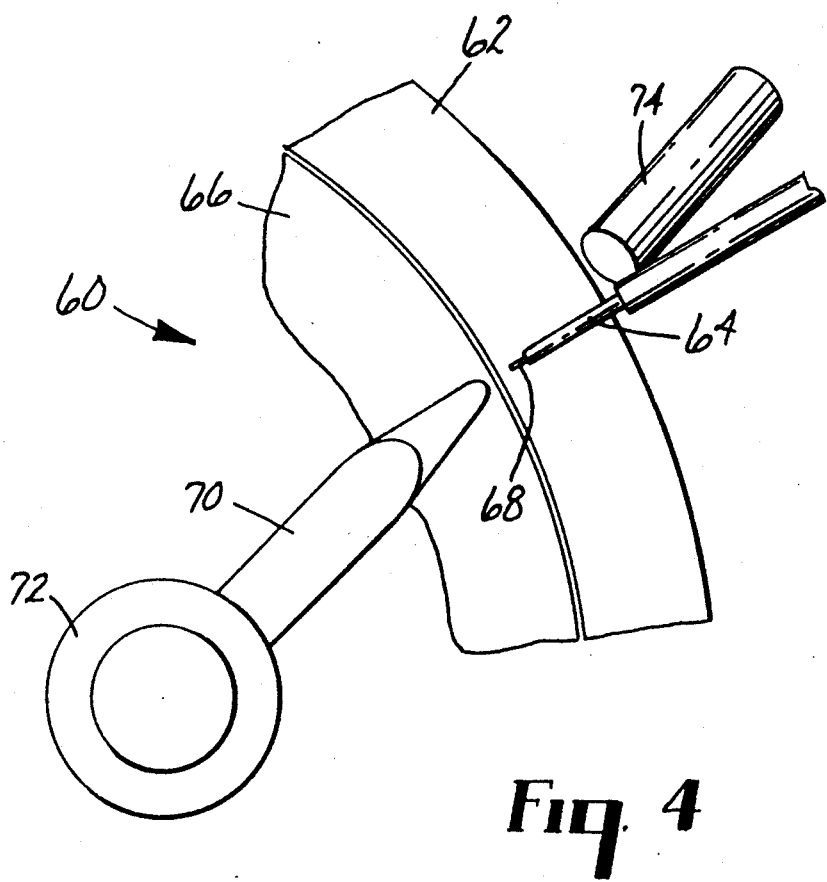
FIG. 4 is a schematic view of an alternative embodiment of the dynamic contact angle measurement system.

FIG. 4 shows an alternative embodiment of the angle measurement apparatus 60 in which a coating 18 is coated on a moving web 62 through a needle 64 such as a syringe needle as the web 62 moves over a backup roller 66. The contact angle can be measured at normal coating speeds. The needle 64 is positioned near the edge of the backup roll 66, and the web 62 is run even with or slightly over the edge of the backup roller 66. The needle 64 coats a narrow stripe having no edge bead. The outlet of the needle 68 of the needle 64 is moved into position adjacent one edge of the backup roller 66.

The bead of coating fluid 18 is observed from the side through a microscope 70. A vernier protractor mount 72 is attached to the eyepiece of the microscope 70 to measure the contact angle. A standard microscope illuminator 74 shining directly past the needle 64 and into the microscope 72 provides a strong backlight for viewing. Alternatively, a video camera records the observations as in the embodiments of FIGS. 1-3. The video camera reduces the total time of the experiment. In another embodiment, a laser and lens system can be used to make traceable images on paper.

Numerous characteristics, advantages, and embodiments of the invention have been described in detail in the foregoing description with reference to the accompanying drawings. However, the disclosure is illustrative only and the invention is not intended to be limited to the precise embodiments illustrated. Various changes and modifications may be effected therein by one skilled in the art without departing from the scope or spirit of the invention.

We claim:

1. An apparatus for measuring the dynamic contact angle of a coating fluid on a coating substrate during coating comprising:
   a rotatable coating wheel;
   a discrete coating substrate segment wrapped around the coating wheel;
   a coating tube having a narrow outlet nozzle, wherein the outlet nozzle produces a coating having no edge bead;
   means for moving the coating fluid through the coating tube;
   means for measuring the contact angle between the coating fluid and the coating substrate.

2. The apparatus of claim 1 wherein the coating tube comprises a syringe.

3. The apparatus of claim 1 wherein the measuring means comprises means for viewing the interface between the coating fluid and the coating substrate in a plane substantially parallel to the axis and the surface of the coating roller, wherein the viewing means comprises a video camera.

4. The apparatus of claim 1 further comprising means for rotating the coating wheel at a surface speed equal to the speed at which the coating fluid is typically coated; and means for pumping the coating fluid through the coating tube.

5. The apparatus of claim 1 further comprising a slide table on which the coating tube is mounted, wherein the slide table slides the coating tube into and out of position for coating on the coating substrate.

6. A method of measuring the dynamic contact angle of a coating fluid on a discrete coating substrate segment during coating comprising the steps of:
   mounting the coating substrate segment around a coating wheel;
   locating the narrow outlet nozzle of a coating tube adjacent the coating wheel;
   rotating the coating wheel at a surface speed equal to the speed at which the coating fluid is typically coated;
   ejecting the coating fluid from the coating tube outlet nozzle onto the coating substrate in a narrow stripe as the coating substrate passes around the coating roller, to produce a coating having no edge bead; and
   measuring the dynamic contact angle of the coating fluid on the coating substrate.

7. The method of claim 6 further comprising the steps of viewing the interface between the coating fluid and the coating substrate in a plane substantially parallel to the axis and the surface of the coating roller; and recording the viewed interface and wherein the measuring step comprises measuring the dynamic contact angle from the recorded interface.

8. An apparatus for measuring the dynamic contact angle of a coating fluid on a coating substrate during coating comprising:

a substrate support;

a coating substrate which travels around the substrate support;

a narrow coating outlet nozzle located adjacent one edge of the substrate support, wherein the outlet nozzle produces a coating having no edge bead;

means for moving the coating fluid through the coating tube;

means for viewing the interface between the coating fluid and the coating substrate in a plane substantially parallel to the axis and the surface of the substrate support; and means for measuring the contact angle between the coating fluid and the coating substrate.

9. The apparatus of claim 8 wherein the substrate support comprises a coating roller and the narrow coating outlet nozzle comprises a narrow tube and the viewing means comprises a video camera.

* * * * *